(12) United States Patent
Weinberg et al.

(10) Patent No.: US 11,709,218 B2
(45) Date of Patent: Jul. 25, 2023

(54) MRI DETECTION OF FREE-RADICALS FROM RADIATION

(71) Applicant: Weinberg Medical Physics, Inc., North Bethesda, MD (US)

(72) Inventors: Irving N. Weinberg, North Bethesda, MD (US); Stanley Thomas Fricke, North Bethesda, MD (US); Aleksandar N. Nacev, Bethesda, MD (US)

(73) Assignee: WEINBERG MEDICAL PHYSICS INC

( * ) Notice: Subject to any disclaimer, the term of this patent is extended or adjusted under 35 U.S.C. 154(b) by 284 days.

(21) Appl. No.: 16/109,264

(22) Filed: Aug. 22, 2018

(65) Prior Publication Data

US 2019/0086502 A1    Mar. 21, 2019

Related U.S. Application Data

(60) Provisional application No. 62/548,641, filed on Aug. 22, 2017.

(51) Int. Cl.
| | | |
|---|---|---|
| *G01R 33/60* | (2006.01) | |
| *A61B 5/05* | (2021.01) | |
| *G01R 33/28* | (2006.01) | |
| *A61N 5/10* | (2006.01) | |
| *G01R 33/385* | (2006.01) | |
| *A61B 5/0515* | (2021.01) | |
| *A61B 5/00* | (2006.01) | |
| *A61B 5/055* | (2006.01) | |

(Continued)

(52) U.S. Cl.
CPC .............. *G01R 33/60* (2013.01); *A61B 5/055* (2013.01); *A61B 5/0515* (2013.01); *A61B 5/4848* (2013.01); *A61N 5/1071* (2013.01); *G01R 33/288* (2013.01); *G01R 33/385* (2013.01); *G01R 33/5601* (2013.01); *A61B 5/14539* (2013.01); *A61N 2005/1055* (2013.01); *A61N 2005/1087* (2013.01); *G01R 33/3808* (2013.01); *G01R 33/4804* (2013.01); *G01R 33/4808* (2013.01); *G01R 33/50* (2013.01); *G01R 33/543* (2013.01)

(58) Field of Classification Search
CPC .... G01R 33/60; G01R 33/288; G01R 33/385; G01R 33/543; G01R 33/4808; G01R 33/5601; G01R 33/3808; G01R 33/4804; G01R 33/50; A61B 5/0515; A61B 5/14539; A61B 5/055; A61B 5/4848; A61N 5/1071; A61N 2005/1087; A61N 2005/1055; A61N 5/1039; A61N 5/1064
See application file for complete search history.

(56) References Cited

U.S. PATENT DOCUMENTS 5,203,332 A *  4/1993  Leunbach .............. G01R 33/62
                                                         324/309
6,198,957 B1*  3/2001  Green .................. A61N 5/1042
                                                          378/65

(Continued)

FOREIGN PATENT DOCUMENTS

WO    WO-2010004464 A1 *  1/2010  ............. A61K 49/18

*Primary Examiner* — Patrick Assouad
*Assistant Examiner* — Haidong Zhang
(74) *Attorney, Agent, or Firm* — Barnes & Thornburg LLP

(57) ABSTRACT

Embodiments now disclosed herein provide an apparatus and method in which free radicals can be detected in a substance by MRI without changing the MRI static field.

16 Claims, 2 Drawing Sheets

(51) Int. Cl.
 *G01R 33/56* (2006.01)
 *G01R 33/54* (2006.01)
 *G01R 33/48* (2006.01)
 *G01R 33/50* (2006.01)
 *G01R 33/38* (2006.01)
 *A61B 5/145* (2006.01)

(56) References Cited

U.S. PATENT DOCUMENTS

| | | | |
|---|---|---|---|
| 8,154,286 B2* | 4/2012 | Weinberg | G01R 33/3852 |
| | | | 324/309 |
| 9,612,308 B2* | 4/2017 | Weinberg | G01R 33/60 |
| 2012/0223711 A1* | 9/2012 | Weinberg | G01R 33/3852 |
| | | | 324/309 |
| 2013/0225974 A1* | 8/2013 | Van Den Brink | A61N 5/1039 |
| | | | 600/411 |
| 2017/0003291 A1* | 1/2017 | Bahado-Singh | A61B 5/4325 |
| 2017/0227617 A1* | 8/2017 | Weinberg | G01R 33/381 |

* cited by examiner

MRI DETECTION OF FREE-RADICALS FROM RADIATION

CROSS REFERENCE AND PRIORITY CLAIM

This patent application claims priority to U.S. Provisional Application Provisional Patent Application No. Patent Application Ser. No. 62/548,641, "MRI DETECTION OF FREE-RADICALS FROM RADIATION," filed Aug. 22, 2017, the disclosure of which being incorporated herein by reference in its entirety.

FIELD

Disclosed embodiments pertain to the assessment of damage from radiation in medical, defense, safety, and other technological fields.

BACKGROUND

Disclosed embodiments represent an extension of work made by the inventors since their earlier patent application Ser. No. 13/475,005, entitled "ULTRA-FAST MAGNETIC FIELD ULTRA-FAST MAGNETIC FIELD FOR ELECTRON PARAMAGNETIC RESONANCE IMAGING USED IN MONITORING DOSE FROM PROTON OR HADRON THERAPY" now issued as U.S. Pat. No. 9,612,308, (incorporated by reference in its entirety).

Prior to that innovation, conventional external beam, radiation therapy was improved by estimating the radiation dose received by the patient based on monitoring by placement of a "phantom" in the expected location of the part of the patient irradiated, wherein the phantom is generally equipped with an instrument (e.g., a dosimeter) that can keep track of the amount of radiation exposure to one or more locations within the phantom.

U.S. Pat. No. 9,612,308 provided the ability to directly assess the presence of free radicals in patients after radiation therapy. More specifically, U.S. Pat. No. 9,612,308 disclosed a method and apparatus for using Magnetic Resonance Imaging (MRI) to detect free-radicals generated by radiation in various materials (including tissue).

SUMMARY

The following presents a simplified summary in order to provide a basic understanding of some aspects of various invention embodiments. The summary is not an extensive overview of the invention. It is neither intended to identify key or critical elements of the invention nor to delineate the scope of the invention. The following summary merely presents some concepts of the invention in a simplified form as a prelude to the more detailed description below.

Similar to U.S. Pat. No. 9,612,308, in accordance with at least one disclosed embodiment, instrumentation and methodologies are provided that enable the direct measurement of free radicals generated in patients as a result of radiation therapy through the use of proton beams and other forms of ionizing radiation. As a result, in accordance with at least one disclosed embodiment, the instrumentation and methodologies may be used in conjunction with radiation therapy to detect, monitor and/or control generation of free radicals in cancerous tissue during such radiation therapy. Similarly, disclosed embodiments implement a method and apparatus for using MRI to detect free-radicals generated by radiation in various materials (including the tissue of a living or deceased subject).

More specifically, disclosed embodiments provide this capability, which has technical utility for the purposes of, for example, depicting the damage caused by radiation therapy to cancer as well as the damage caused to normal cells.

However, unlike U.S. Pat. No. 9,612,308, embodiments now disclosed herein provide an apparatus and method in which free radicals can be detected by MRI without changing the MRI static field.

BRIEF DESCRIPTION OF THE FIGURES

The detailed description particularly refers to the accompanying figures in which.

DETAILED DESCRIPTION

As disclosed in U.S. Pat. No. 9,612,308, free radicals generated by radiation can be detected by shifting the MRI static field from a low value (at which free electrons can be excited magnetically) to a higher field (at which the magnetic moments of protons can be assessed), and taking advantage of the ability of the free electrons to transfer magnetization to protons.

Embodiments now disclosed herein provide an apparatus and method in which free radicals can be detected by MRI without changing the MRI static field.

The description of specific embodiments is not intended to be limiting of the present invention. To the contrary, those skilled in the art should appreciate that there are numerous variations and equivalents that may be employed without departing from the scope of the present invention. Those equivalents and variations are intended to be encompassed by the present invention.

In the following description of various invention embodiments, reference is made to the accompanying drawings, which form a part hereof, and in which is shown, by way of illustration, various embodiments in which the invention may be practiced. It is to be understood that other embodiments may be utilized and structural and functional modifications may be made without departing from the scope and spirit of the present invention.

As explained above, in accordance with at least one disclosed embodiment, instrumentation and methodologies are provided that enable the direct measurement of free radicals generated in patients as a result of radiation therapy through the use of proton beams and other forms of ionizing radiation. As a result, in accordance with at least one disclosed embodiment, the instrumentation and methodologies may be used in conjunction with radiation therapy to detect, monitor and/or control generation of free radicals in cancerous tissue during such radiation therapy.

Conventionally, it is known that radiation therapy produces reactive oxygen species, termed "excited" for the purposes of this description. The term "excited" also includes free radicals, ionized hydrogen, or other such materials that are not in their stable state. The reduction of molecular oxygen $O_2 + e^-$ where a free electron associates to the $O_2$ molecule creates the superoxide $O_2^-$ which is the precursor of other reactive oxygen species such as:

$$O_2^{-2}, H_2O_2, OH, OH^-.$$

Both $O_2$, $O_2^-$ are paramagnetic. The paramagnetic superoxide and/or the lone dioxide may constitute a temporary endogenous MRI tissue contrast agent caused by the application of radiation. Such application of radiation can be experienced by a subject's tissues during radiation therapy, or exposure to unwanted radiation (such as from a "dirty bomb"). The mechanism of contrast may be due to magnetic interactions between protons assessed by MRI and neighboring protons and/or electrons.

Figure 1:
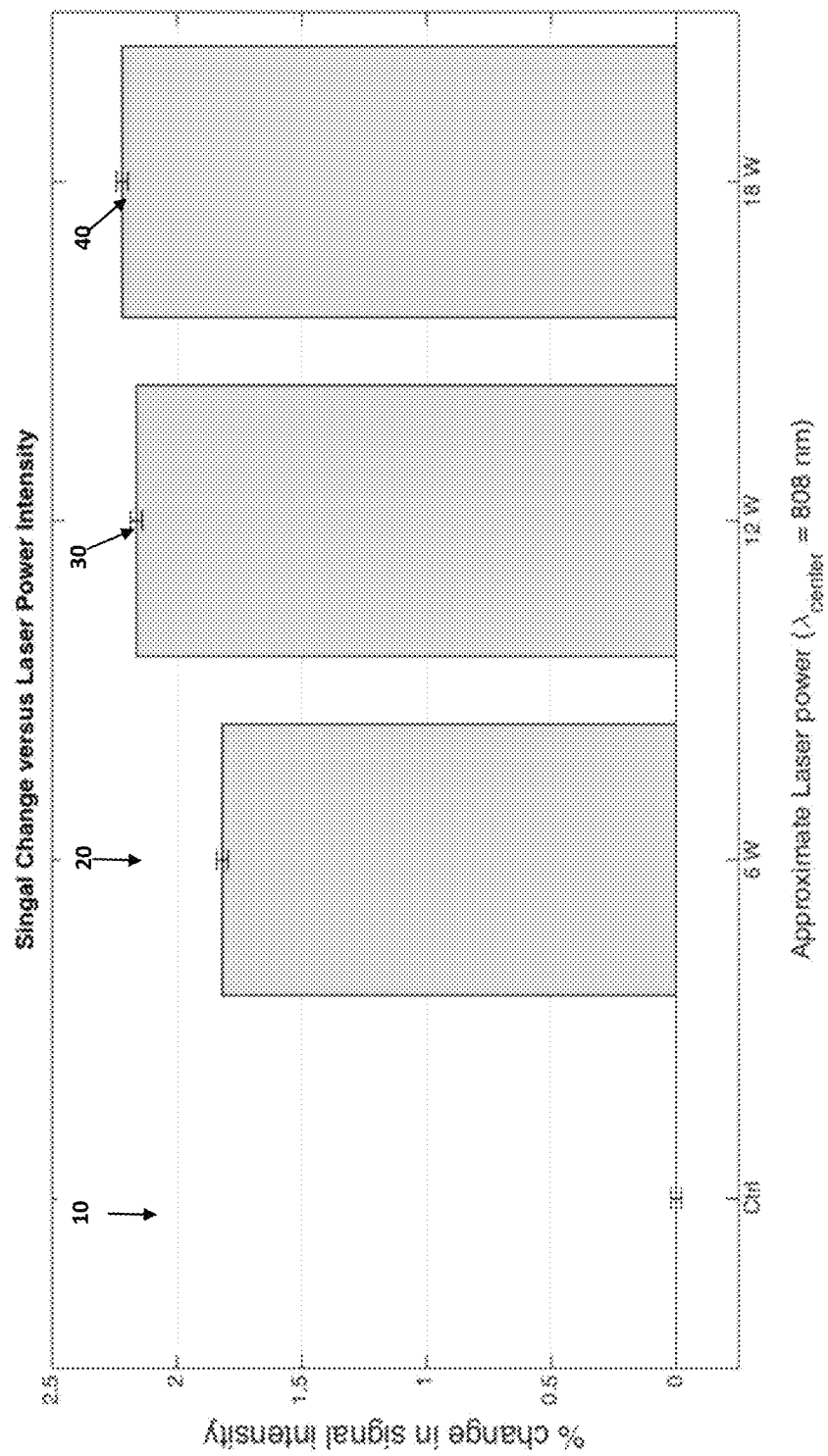
FIG. 1 illustrates the effects of increasing magnetic resonance signal without and with increasing levels of exposure of an aqueous solution of copper sulfate to light from a laser.

These magnetic interactions may affect the decay properties of the protons assessed with MRI that generate contrast to unaffected protons, made visible with pulse sequences as in FIG. 1.

More specifically, FIG. 1 illustrates increasing magnetic resonance signal without 10 and with increasing levels of exposure 20, 30, 40 of an aqueous solution of copper sulfate to light from a laser, which is believed to be related to the generation of superoxide and/or free electrons in the solution.

Alternatively, the presence of free radicals or superoxide or ionized hydrogen species may affect the pH of a solution or tissue. Such pH changes may be measured with MRI, as is known from the 2012 publication in the journal Contrast Media Molecular Imaging by Vipul R. Sheth et al entitled "Improved pH measurements with a single PARACEST MRI contrast agent," incorporated by reference herein.

For the purposes of this description, the term "contrast" includes the presence of a signal detectable with MRI that is different in a portion of material exposed to radiation as compared to a portion of material that has not been exposed to radiation.

In accordance with at least some disclosed embodiments, it should be understood that the presence of MRI contrast relating to prior exposure of material to radiation may be used to control or alter subsequent exposure of the material to radiation, for example, as needed to implement and/or modify a radiation planning protocol prescribed for treatment of cancer. It is known that radiation therapy may not always proceed according to the radiation planning protocol, for example due to motion of a body part or to filling of some body parts with fluid or other substances that were not taken into account during the radiation planning process. An example of such discrepancy was described in the 2007 publication in the journal International Journal of Radiation Oncology and Biological Physics, entitled "Patient Study of In Vivo Verification of Beam Delivery and Range, Using Positron Emission Tomography and Computed Tomography Imaging After Proton Therapy" by K Parodi et al., incorporated by reference herein.

It should be understood that the modification of continued radiation therapy to a body part in response to the information provided by the MRI as to dose may potentially result in more effective destruction of cancers and/or less harm to non-cancerous tissues.

The signals from excited species may decay rapidly (for example in milliseconds). These quickly decaying signals would therefore require fast imaging sequences to localize the signals in space. Examples of fast imaging sequences that could be used include: 1) gradient echo imaging sequences with an Echo Time (TE) that is less than a millisecond; 2) spin echo based imaging sequences that have an echo time less than a millisecond; and 3) single point imaging schemes that acquire frequency information at less than a millisecond. Most of these fast MRI sequences will require gradient pulses that are applied and removed much faster than the echo time.

In these cases, the gradient pulses may be on the order of a 100-400 microseconds. These gradient pulses may then need to rise and fall with a speed that is faster than 10 microseconds so as to limit peripheral nerve stimulation. These fast imaging sequences may be better able to detect the quickly decaying signals when compared with a conventionally known, slow MRI scanner.

Figure 2:
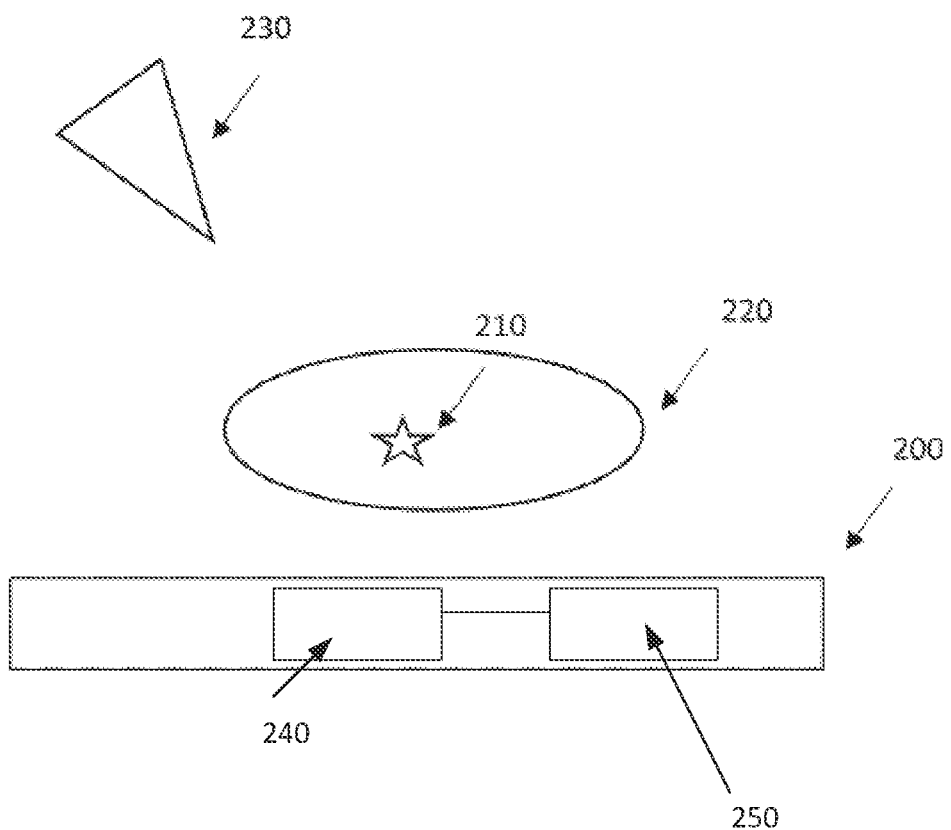
FIG. 2 illustrates a single-sided MRI system assessing the presence of excited materials in a body part or other structure or substance.

FIG. 2 illustrates a single-sided MRI system 200 assessing the presence of excited materials 210 (for example, superoxide species) in a subject's body part or other structure or substance 220, wherein the excited materials are generated by a radiation source 230.

It should be understood that the apparatus 200 for applying magnetic fields for imaging and/or manipulation may use electropermanent magnets, as taught by Irving Weinberg in US Pat. Pub. 20170227617, corresponding to U.S. patent application Ser. No. 15/427,426, entitled "METHOD AND APPARATUS FOR MANIPULATING ELECTROPERMANENT MAGNETS FOR MAGNETIC RESONANCE IMAGING AND IMAGE GUIDED THERAPY," incorporated herein by reference.

Such electropermanent magnets may at one or more times create a magnetic field configuration for imaging of a subject's body part or other material. It should be understood that the imaging capability may be through magnetic resonance imaging methods.

It should be understood that the term "radiation" includes the case of ionizing radiation. Ionizing radiation is typically employed in radiation therapy.

It should be understood that one or more magnetic fields applied by system 200 to a subject's tissue or body part 220 may be so rapidly applied so as not to cause unpleasant nerve stimulation, as taught by Irving Weinberg in issued U.S. Pat. No. 8,154,286, entitled "APPARATUS AND METHOD FOR DECREASING BIO-EFFECTS OF MAGNETIC FIELDS" and patent applications related by priority claim, by Irving Weinberg, which are all incorporated herein by reference.

It should be understood that the term "subject" refers to and includes humans and other animals, whether they be alive or once-living. Similarly, the term "body part or other structure" may mean a tissue-containing structure in a living or once-living organism such as a human or other animal.

It should be understood that the measurement of the effect of radiation exposure on a material or substance as described herein, may occur during exposure to ongoing radiation, or after exposure to radiation.

It should be understood that MRI of a substance is generally described as a set of at least one magnetic coil disposed adjacent or near to a substance. The term "near" may be less than one meter, less than 10 meters, or less than 100 meters. It is understood that a computer 250 is generally connected to the at least one coil 240 for collection, reconstruction, display, and/or interpretation of data from the at least one coil. It is understood that the MRI may be one-, two-, or three-sided, or may surround the substance of interest.

It should be understood that disclosed embodiments may also be used to assess whether materials have been irradiated, as may have occurred in an undesirable situation such as a "dirty bomb" or a desirable situation such as sterilization of medical materials or foodstuffs.

It should be understood that various connections are set forth between elements in the following description; however, these connections in general, and, unless otherwise specified, may be either direct or indirect, either permanent or transitory, and either dedicated or shared, and that this specification is not intended to be limiting in this respect.

While this invention has been described in conjunction with the specific embodiments outlined above, it is evident that many alternatives, modifications and variations will be apparent to those skilled in the art. Accordingly, the various embodiments of the invention, as set forth above, are intended to be illustrative, not limiting. Various changes may be made without departing from the spirit and scope of the invention.

Additionally, it should be understood that the functionality described in connection with various described components of various invention embodiments may be combined or separated from one another in such a way that the architecture of the invention is somewhat different than what is expressly disclosed herein. Moreover, it should be understood that, unless otherwise specified, there is no essential requirement that methodology operations be performed in the illustrated order; therefore, one of ordinary skill in the art would recognize that some operations may be performed in one or more alternative order and/or simultaneously.

Various components of the invention may be provided in alternative combinations operated by, under the control of or on the behalf of various different entities or individuals.

Further, it should be understood that, in accordance with at least one embodiment of the invention, system components may be implemented together or separately and there may be one or more of any or all of the disclosed system components. Further, system components may be either dedicated systems or such functionality may be implemented as virtual systems implemented on general purpose equipment via software implementations.

It should be understood that components disclosed herein may be used in conjunction with, as described above, other components, for example a computer processor. In addition, the disclosed apparatus may include, utilize or be used in conjunction with a power supply and/or coils for generating magnetic and/or electromagnetic fields, in order to generate an electrical field. Thus, although not shown in detail herein, it should be understood that the disclosed embodiments may be used in conjunction with a support structure that may hold coils for exciting materials, wherein the support structure includes coils used to apply the electric field as well as, optionally, an imaging system to enable positioning and/or monitoring of the excited materials. Moreover, it should be understood that an associated display system is not shown but should be understood to be present in order to view images produced by the imaging system.

It should be understood that the operations explained herein may be implemented in conjunction with, or under the control of, one or more general purpose computers running software algorithms to provide the presently disclosed functionality and turning those computers into specific purpose computers.

Moreover, those skilled in the art will recognize, upon consideration of the above teachings, that the above exemplary embodiments may be based upon use of one or more programmed processors programmed with a suitable computer program. However, the disclosed embodiments could be implemented using hardware component equivalents such as special purpose hardware and/or dedicated processors. Similarly, general purpose computers, microprocessor based computers, micro-controllers, optical computers, analog computers, dedicated processors, application specific circuits and/or dedicated hard wired logic may be used to construct alternative equivalent embodiments.

Moreover, it should be understood that control and cooperation of the above-described components may be provided using software instructions that may be stored in a tangible, non-transitory storage device such as a non-transitory computer readable storage device storing instructions which, when executed on one or more programmed processors, carry out the above-described method operations and resulting functionality. In this case, the term non-transitory is intended to preclude transmitted signals and propagating waves, but not storage devices that are erasable or dependent upon power sources to retain information.

Those skilled in the art will appreciate, upon consideration of the above teachings, that the program operations and processes and associated data used to implement certain of the embodiments described above can be implemented using disc storage as well as other forms of storage devices including, but not limited to non-transitory storage media (where non-transitory is intended only to preclude propagating signals and not signals which are transitory in that they are erased by removal of power or explicit acts of erasure) such as for example Read Only Memory (ROM) devices, Random Access Memory (RAM) devices, network memory devices, optical storage elements, magnetic storage elements, magneto-optical storage elements, flash memory, core memory and/or other equivalent volatile and non-volatile storage technologies without departing from certain embodiments. Such alternative storage devices should be considered equivalents.

While certain illustrative embodiments have been described, it is evident that many alternatives, modifications, permutations and variations will become apparent to those skilled in the art in light of the foregoing description. Accordingly, the various embodiments of, as set forth above, are intended to be illustrative, not limiting. Various changes may be made without departing from the spirit and scope of the invention.

As a result, it will be apparent for those skilled in the art that the illustrative embodiments described are only examples and that various modifications can be made within the scope of the invention as defined in the appended claims.

What is claimed:

1. An apparatus for measurement of exposure of a substance to radiation, the apparatus comprising:
at least one magnetic coil positioned near the substance and operated to collect one or more signals from excited species in the substance during or after exposure of the substance to ionizing radiation, and
an MRI system that includes the at least one magnetic coil,
wherein the MRI system includes a plurality of electropermanent sections,
wherein the MRI system detects radiation exposure by assessing signals from excited species that generate contrast in the substance, wherein the excited species are free radicals, superoxide, or ionized hydrogen species, wherein the excited species are produced by exposing the substance to the ionizing radiation,
wherein the MRI has pulse sequences that include at least one pulse whose rise-time, fall-time, or duration are less than 10 microseconds long,
wherein the MRI system is sensitive to signals from excited species in the substance and wherein the contrast is generated between a portion of the substance that has been exposed and a portion of the substance that has not been exposed to the ionizing radiation, and wherein the control of subsequent exposure is based on the contrast.

2. The apparatus of claim 1, further comprising a computer coupled to the at least one magnetic coil, controlling operation of the at least one magnetic coil and analyzing data collected from the one or more signals from excited species in the substance.

3. The apparatus of claim 1, further comprising a source of radiation controlled to expose the substance to radiation for radiation therapy.

4. The apparatus of claim 3, wherein continued exposure of the substance to radiation is performed in response to the signals from excited species in the substance.

5. The apparatus of claim 1, wherein the substance is a subject's body part.

6. The apparatus of claim 1, wherein the MRI system is a single-sided MRI system.

7. The apparatus of claim 1, wherein the substance is part of a subject, and wherein the at least one magnetic coil generates a magnetic field that rises or falls in such short a time as not to cause nerve stimulation of the subject.

8. The apparatus of claim 1, wherein the at least one magnetic coil generates a magnetic field that rises or falls in less than 10 microseconds.

9. A method of assessing radiation exposure to a substance using MRI, the method comprising:
   positioning at least one magnetic coil near the substance; and
   operating the at least one magnetic coil to collect one or more signals from excited species in the substance during or after exposure of the substance to ionizing radiation, wherein the excited species are free radicals, superoxide, or ionized hydrogen species, wherein the excited species are produced by exposing the substance to the ionizing radiation, and
   controlling subsequent exposure of the substance to radiation exposure based on detected prior exposure,
   wherein the at least one magnetic coil is part of an MRI system,
   wherein the MRI system includes a plurality of electropermanent sections,
   wherein the MRI system generates pulse sequences capable of assessing signals from excited species in the substance in which the signals decay within ten milliseconds,
   wherein the MRI has pulse sequences that include at least one pulse whose rise-time, fall-time, or duration are less than 10 microseconds long,
   wherein the MRI system is sensitive to signals from excited species in the substance and wherein the contrast is generated between a portion of the substance that has been exposed and a portion of the substance that has not been exposed to the ionizing radiation, and wherein the control of subsequent exposure is based on the contrast.

10. The method of claim 9, further comprising controlling the at least one magnetic coil using a computer coupled to the at least one magnetic coil, and analyzing data collected from the one or more signals.

11. The method of claim 9, further comprising exposing the substance to radiation for radiation therapy.

12. The method of claim 11, further comprising modifying continued exposure of the substance to radiation in response to the signals from the excited species in the substance.

13. The method of claim 9, wherein the MRI system is a single-sided MRI system.

14. The method of claim 9, wherein the substance is a subject's body part.

15. The method of claim 9, wherein the substance is part of a subject, and wherein the at least one magnetic coil generates a magnetic field that rises or falls in such short a time as not to cause nerve stimulation of the subject.

16. The method of claim 9, wherein the at least one magnetic coil generates a magnetic field that rises or falls in less than 10 microseconds.

* * * * *